(12) United States Patent
Beaupré

(10) Patent No.: US 11,006,972 B2
(45) Date of Patent: May 18, 2021

(54) ACTUATION MECHANISM AND ULTRASONIC SURGICAL INSTRUMENT

(71) Applicants: REACH SURGICAL INC., Tianjin (CN); CHINA SURGICAL (Shanghai) CORPORATION, Shanghai (CN)

(72) Inventor: Jean Beaupré, Cincinnati, OH (US)

(73) Assignees: Reach Surgical Inc., Tianjin (CN); China Surgical (Shanghai) Corporation, Shanghai (CN)

( * ) Notice: Subject to any disclaimer, the term of this patent is extended or adjusted under 35 U.S.C. 154(b) by 154 days.

(21) Appl. No.: 15/923,632

(22) Filed: Mar. 16, 2018

(65) Prior Publication Data

US 2018/0199958 A1    Jul. 19, 2018

Related U.S. Application Data

(63) Continuation of application No. PCT/CN2015/089703, filed on Sep. 16, 2015.

(51) Int. Cl.
*A61B 17/32* (2006.01)
*A61B 17/29* (2006.01)
*A61B 17/00* (2006.01)

(52) U.S. Cl.
CPC .......... *A61B 17/320092* (2013.01); *A61B 2017/00371* (2013.01); *A61B 2017/00384* (2013.01); *A61B 2017/2912* (2013.01); *A61B 2017/2916* (2013.01); *A61B 2017/2919* (2013.01); *A61B 2017/2925* (2013.01); *A61B 2017/320094* (2017.08)

(58) Field of Classification Search
CPC .. A61B 2017/00371; A61B 2017/2912; A61B 2017/2916; A61B 2017/2919; A61B 2017/320094; A61B 2017/2925; A61B 2017/00384
See application file for complete search history.

(56) References Cited

U.S. PATENT DOCUMENTS

| | | | |
|---|---|---|---|
| 5,605,272 A | 2/1997 | Witt et al. | |
| 2006/0097026 A1* | 5/2006 | Shelton, IV | A61B 17/0682 227/175.1 |
| 2010/0152790 A1 | 6/2010 | Hestad | |
| 2010/0264193 A1* | 10/2010 | Huang | A61B 17/07207 227/176.1 |
| 2011/0087209 A1 | 4/2011 | Boudreaux et al. | |
| 2011/0087220 A1* | 4/2011 | Felder | A61B 18/1445 606/42 |
| 2011/0190809 A1 | 8/2011 | Mohan et al. | |
| 2011/0290853 A1 | 12/2011 | Frederick | |

(Continued)

*Primary Examiner* — George J Ulsh
*Assistant Examiner* — Andrew P. Restaino
(74) *Attorney, Agent, or Firm* — Arent Fox LLP; Michael Fainberg

(57) ABSTRACT

It is disclosed an actuation mechanism for performing an action, where the actuation mechanism comprises: a first movable trigger assembly having a first trigger; a second movable trigger assembly have a second trigger, where the first trigger is movable independently with respect to the second trigger during a portion of movement of the first trigger and/or the second trigger; and a driving member in engagement with the first trigger assembly and the second trigger assembly, respectively, wherein, the first trigger assembly and the second trigger assembly are applied different mechanical advantages.

18 Claims, 6 Drawing Sheets

(56) References Cited

U.S. PATENT DOCUMENTS

| | | |
|---|---|---|
| 2011/0295269 A1 | 12/2011 | Swensgard |
| 2013/0103023 A1 | 4/2013 | Monson et al. |
| 2014/0005682 A1 | 1/2014 | Worrell |
| 2015/0272602 A1* | 10/2015 | Boudreaux ........ A61B 17/2841 606/167 |
| 2016/0106456 A1 | 4/2016 | Xue et al. |
| 2017/0055970 A1* | 3/2017 | Hess .................. A61B 17/2909 |

* cited by examiner

ACTUATION MECHANISM AND ULTRASONIC SURGICAL INSTRUMENT

CROSS-REFERENCE TO RELATED APPLICATION

This application is a continuation of International Application No. PCT/CN2015/089703 filed on Sep. 16, 2015. The entire disclosure of the above application is incorporated herein by reference.

TECHNICAL FIELD

The present invention relates generally to medical device, and more specifically to an actuation mechanism and an ultrasonic surgical instrument using the same.

BACKGROUND

Ultrasonic surgical system has been used for quite some time in cutting, coagulation and/or dissection of tissue during various medical procedures, such as open and endoscopic surgeries, due to its good vessel sealing and small damages to tissue. The typical ultrasonic surgical system includes various components, such as generator, ultrasonic transducer, ultrasonic surgical instrument, foot switch, etc. Typically, the ultrasonic transducer is adapted to convert electrical energy that is typically supplied by the generator, into mechanical energy, for example, into vibration motion, which is further transmitted to the ultrasonic surgical instrument. Mechanical vibratory energy will be further amplified and transmitted by the ultrasonic surgical instrument and eventually be transmitted to the tissue, so as to cutting, coagulation and/or dissection of tissue through intracellular water vaporization, protein hydrogen bonds break, cell disintegration, etc.

The ultrasonic surgical instrument of prior art typically includes a handle portion, an end-effector and a clamping assembly, where the handle portion is provided with one trigger. Operator can grasp the handle portion and rotate the trigger, so as to manipulate the clamping assembly disposed on the distal portion of the instrument to open or close, for clamping, grasping, dissecting or holding tissue or vessel, such that the end-effector of the ultrasonic surgical instrument can be used for cutting, coagulation and/or dissection of tissue or vessels.

SUMMARY

In one aspect, the present disclosure provides an actuation mechanism for performing an action, wherein, the actuation mechanism comprises: a first movable trigger assembly having a first trigger; a second movable trigger assembly have a second trigger, wherein the first trigger is movable independently with respect to the second trigger during a portion of movement of the first trigger and/or the second trigger; and a driving member in engagement with the first trigger assembly and the second trigger assembly, respectively, wherein, the first trigger assembly and the second trigger assembly are applied different mechanical advantages.

In another aspect, the present disclosure provides an ultrasonic surgical instrument comprises an actuation mechanism, wherein, the actuation mechanism comprises: a first movable trigger assembly having a first trigger; a second movable trigger assembly have a second trigger, wherein the first trigger is movable independently with respect to the second trigger during a portion of movement of the first trigger and/or the second trigger; and a driving member in engagement with the first trigger assembly and the second trigger assembly, respectively, wherein, the first trigger assembly and the second trigger assembly are applied different mechanical advantages.

In a further aspect, the present disclosure further provides an actuation mechanism for performing action, wherein, the actuation mechanism comprises: a first movable trigger assembly having a first trigger; a second movable trigger assembly having a second trigger, wherein, the first trigger is movable independently with respect to the second trigger during a portion of movement of the first trigger and/or the second trigger; a driving member in engagement with the first trigger assembly and the second trigger assembly, respectively; and a first link, through which the second trigger assembly is engaged with the driving member.

Figure 1:
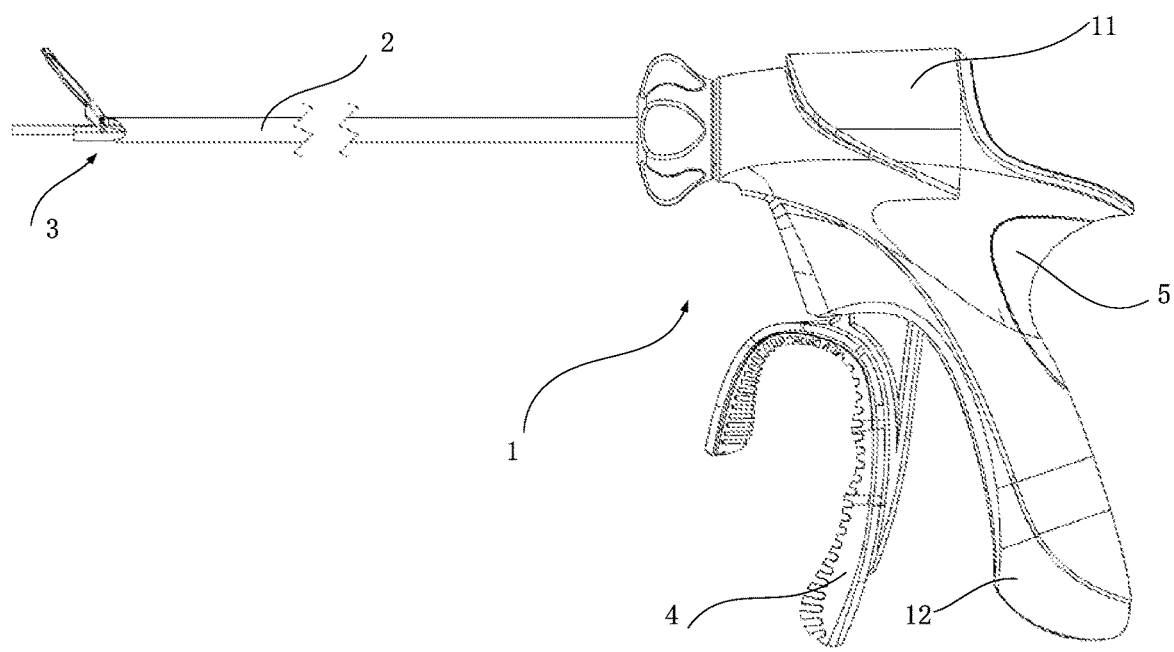
FIG. 1 illustrates an ultrasonic surgical instrument embodiment of the present disclosure.

Reference numerals: 1—handle portion, 2—elongated body 2, 3—clamping assembly, 4—first trigger, 5—second trigger, 6—biasing member, 7—second link, 8—first link, 9—driving member, 10—pivot, 11—handle body, 12—stationary handle, 13—third link, 41—first pivot, 42—aperture, 43—protrusion, 51—second pivot.

DETAILED DESCRIPTION

The technical solutions according to the embodiments of the present disclosure will be described below in details with reference to the figures. Moreover, as used herein, the term "distal" will refer to the portion of the instrument that is farther from the operator and the term "proximal" will refer to the portion of the instrument that is closer to the operator. The following detailed description describes examples of embodiments of the present disclosure solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present disclosure.

It is provided in one of the embodiments of the present disclosure that an actuation mechanism for performing action and an ultrasonic surgical instrument. Referring to FIGS. 2-5, the actuation mechanism comprises a first trigger assembly and a second trigger assembly, both of which are movable. The first trigger assembly is provided with a first trigger 4, and the second trigger assembly is provided with a second trigger 5, where the first trigger may be movable independently with respect to the second trigger during a portion of movement of the first trigger and/or the second trigger. The actuation mechanism further comprises a driving member 9 that is engaged with the first trigger assembly and the second trigger assembly, respectively; the first trigger assembly and the second trigger assembly are applied different mechanical advantages.

More specifically, the first trigger assembly includes the first trigger 4 and a first mechanical advantage mechanism, and the second trigger assembly includes the second trigger 5 and a second mechanical advantage mechanism.

In one of the embodiments of the present disclosure, forces applied on the first trigger 4 and the second trigger 5 may be delivered to the driving member 9 through the rotatable first and second triggers 4, 5 and the first and second mechanical advantage mechanisms, respectively. More specifically, the first mechanical advantage mechanism is engaged with the first trigger 4, adapted for delivering force applied on the first trigger 4 to the driving member 9. The second mechanical advantage mechanical is engaged with the second trigger 5, adapted for delivering force applied on the second trigger 5 to the driving member 9, so as to amplify the force, which amplifying output force of the entire actuation mechanism. It should be understood that the mechanical advantage mechanism may not be designed limited to amplify force from the first trigger 4 or the second trigger 5, it may also be designed for diminishing the force or only equivalent transmitting.

Further, the mechanical advantage of the second trigger assembly is determined by the position of the first trigger 4. Here term "mechanical advantage" refers to the ratio of an output force to an input force of a mechanical system. Taking a lever system as example, which may be one of the most common mechanical advantage mechanisms, the mechanical advantage thereof refers to a ratio of an input force applied on one end to an output force from the other end of the bar. Structures of embodiments of the present disclosure will be illustrated in details hereinafter.

Figure 9:
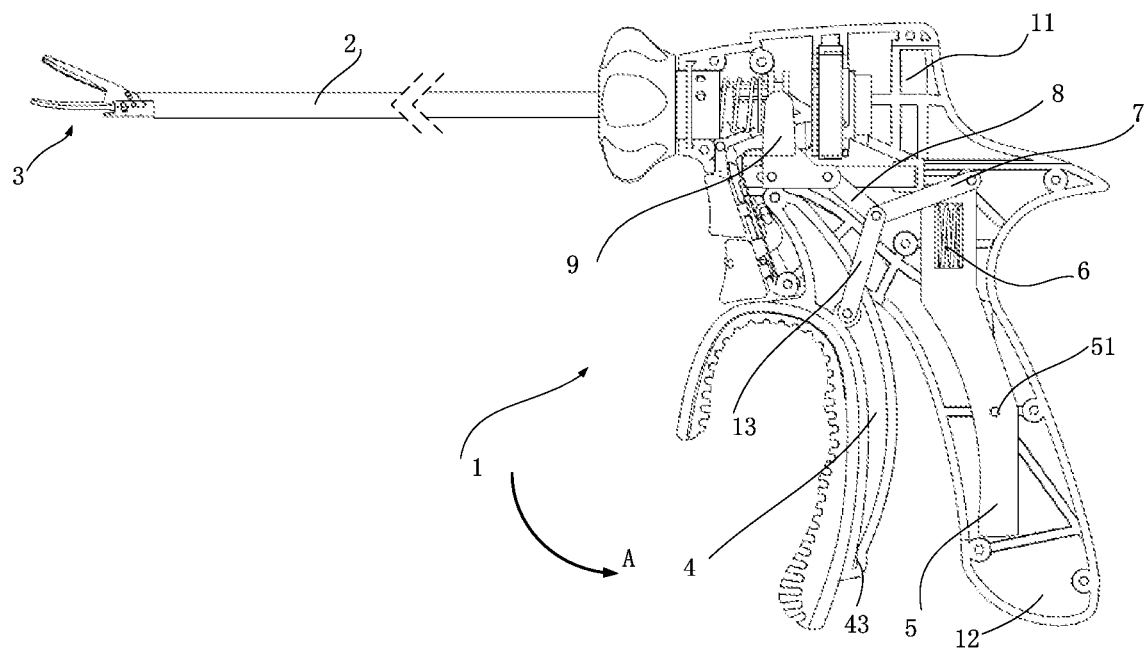
FIG. 9 illustrates an ultrasonic surgical instrument of yet another embodiment of the present disclosure, in free state.
Figure 10:
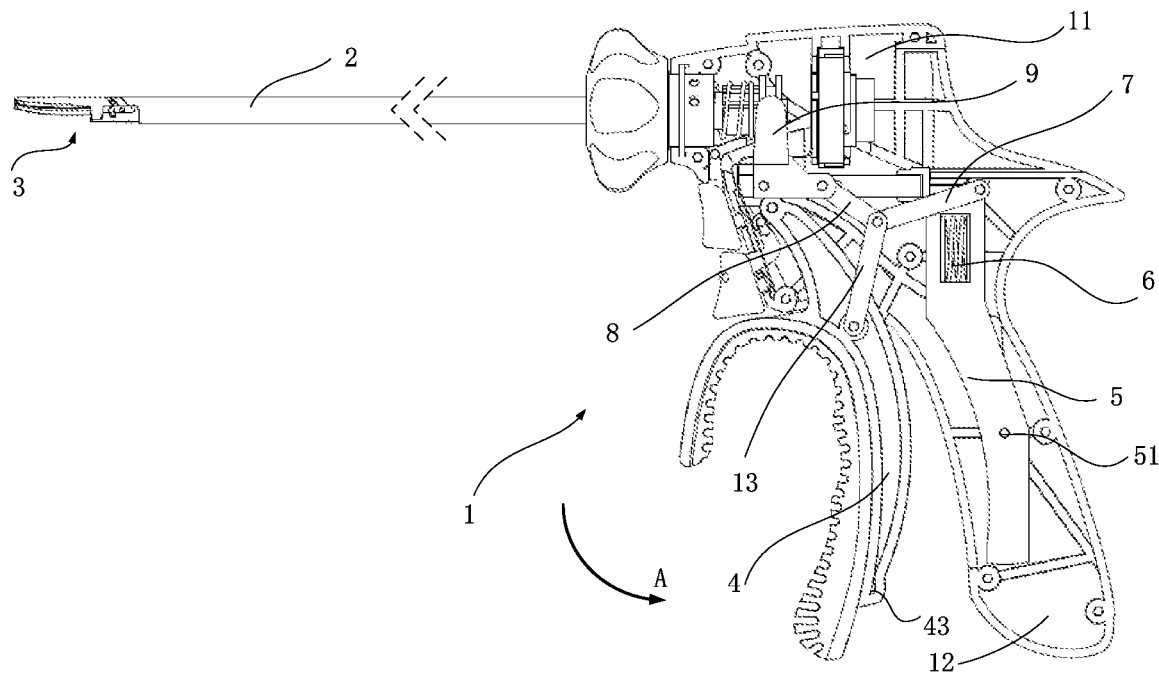
FIG. 10 illustrates schematic view of the ultrasonic surgical instrument of yet another embodiment, with the clamping assembly closed.
Figure 11:
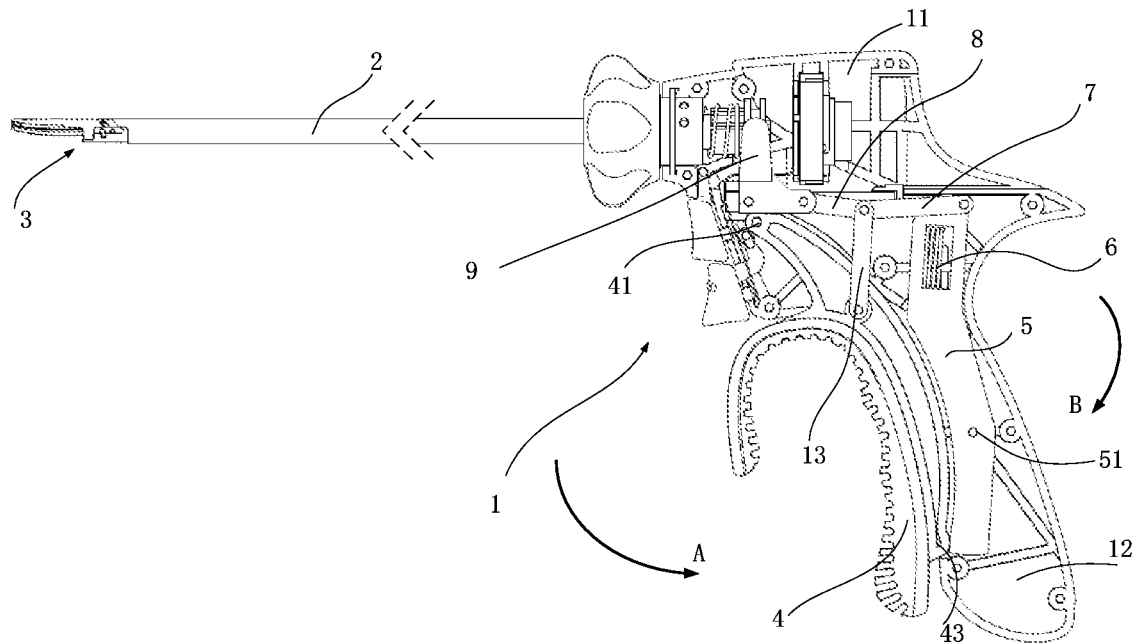
FIG. 11 illustrates schematic view of the ultrasonic surgical instrument of yet another embodiment of the disclosure, with the second trigger being rotated.

In one embodiment of the present disclosure, referring to FIG. 1, it is provided an ultrasonic surgical instrument provided with a handle portion 1, an elongated body 2 and a clamping assembly 3. The handle portion 1 is provided with a handle body 11 and a stationary handle 12, and the clamping assembly 3 and the elongated body 2 may be rotated about a longitudinal axis (indicated by arrow C) of the instrument with respect to the handle portion 1. The position of the first trigger 4 and the second trigger 5 may be arranged according to various requirements. For example, as shown in FIGS. 2-8, the first trigger 4 and the second trigger 5 are arranged on opposing sides of the handle portion 1, respectively. More specifically, the first trigger 4 and the second trigger 5 are arranged on either side of the stationary handle 12 of the handle portion 1, both of which may be contacted with an operator when being grasped. For example, the first trigger 4 and the second trigger 5 can be contacted by fingers (except thumb) and portion between thumb and index finger. Alternatively, the first trigger 4 is arranged on one side of the stationary handle 12 of the handle portion 1, while the second trigger 5 is arranged inside the handle 12 of the handle portion 1, as shown in FIGS. 9-11, where only first trigger 4 may be contacted with the operator when being grasped.

By using different mechanical advantage mechanisms, forces applied on the first trigger 4 and the second trigger 5 may be amplified to different values, respectively, where mechanical advantage of the second trigger assembly may be determined or controlled by the position of the first trigger assembly. More specifically, referring to FIG. 2, the actuation mechanism further comprises a pivot 10, a first link 8 and a second link 7, where the first link 8 is engaged with the second link 7 via the pivot 10. Further, the distal end of the first link 8 is engaged with the driving member 9 that slidably arranged in the ultrasonic surgical instrument. The proximal end of the second link 7 is engaged with the second trigger 5, and the pivot 10 is engaged with the first trigger 4 so that when the first trigger 4 rotates, it may push the pivot 10, and the first link 8 may push the driving member 9 and/or the second trigger 7 may push the second trigger 6; or when the second trigger 5 rotates, it may pushes the second link 7 and the first link 8 may push the driving member 9.

Figure 2:
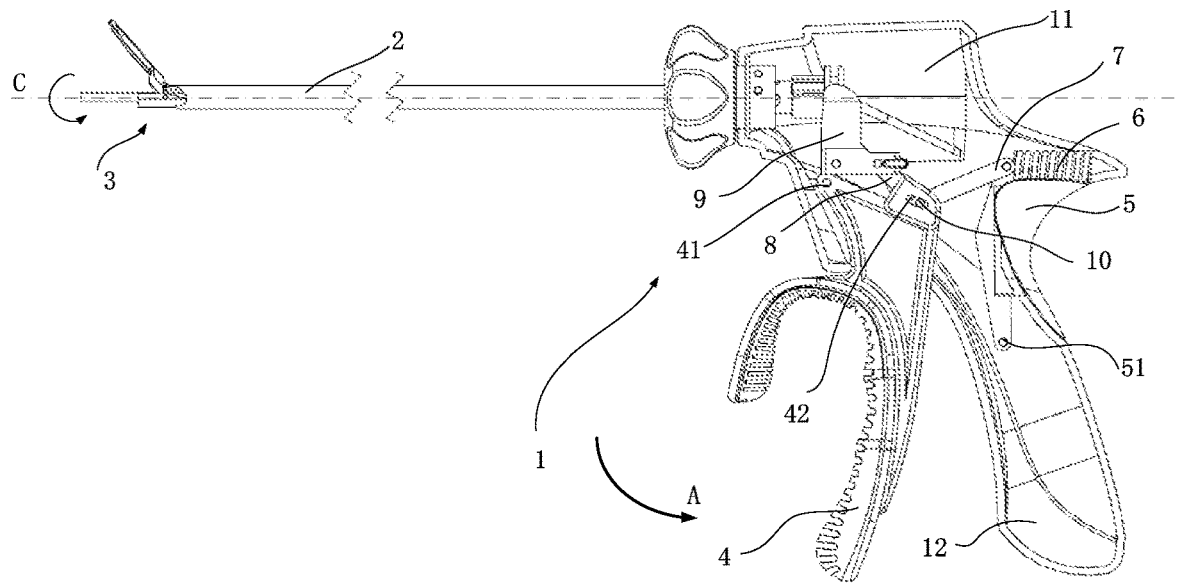
FIG. 2 illustrates structures of the ultrasonic surgical instrument of the present disclosure.
Figure 3:
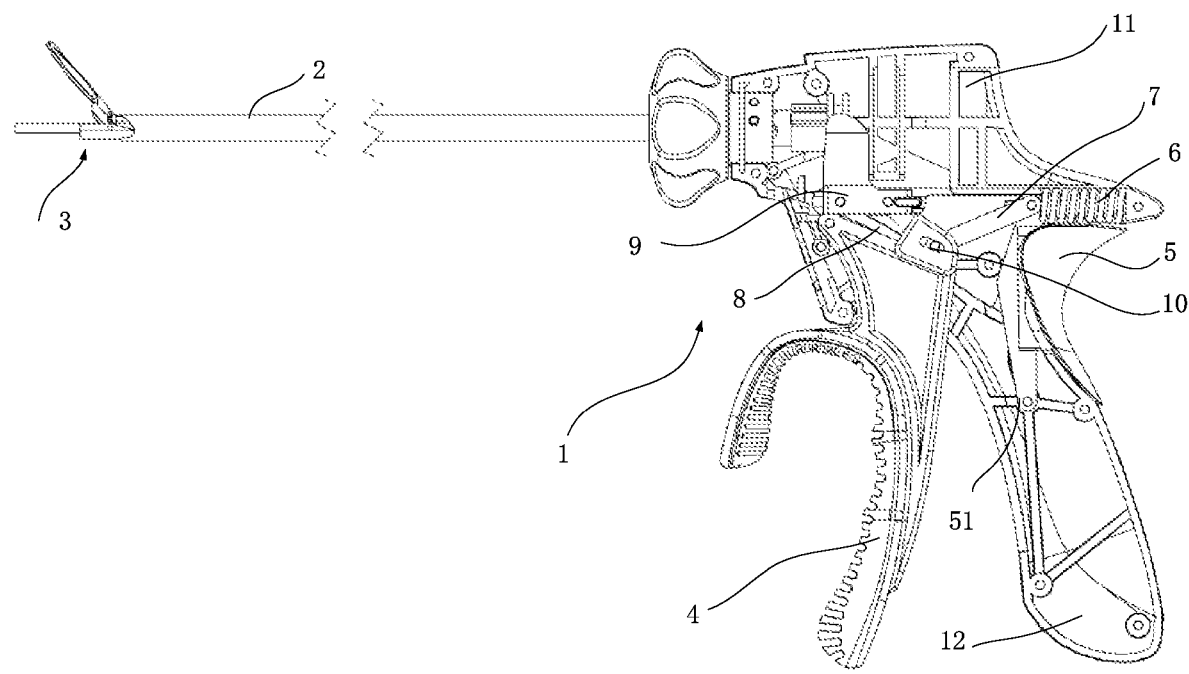
FIG. 3 illustrates the ultrasonic surgical instrument of one embodiment of the present disclosure in free state.
Figure 4:
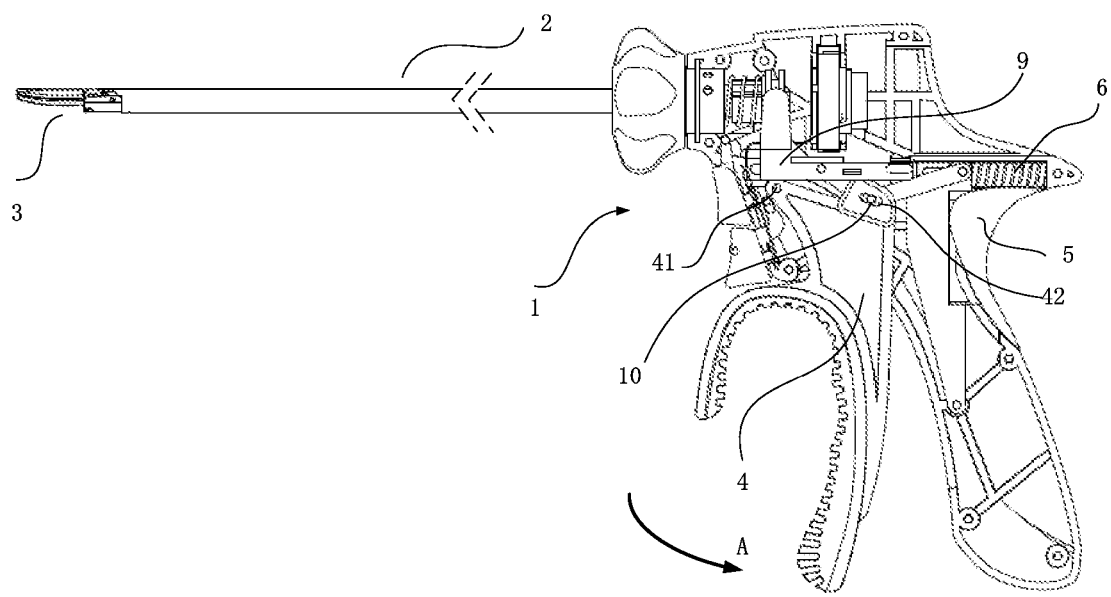
FIG. 4 illustrates schematic view of the ultrasonic surgical instrument of one embodiment, with the clamping assembly closed.

The driving member 9 is configured to actuate the clamping assembly 3 to open or close through the elongated body 2. More specifically, a sliding member, for example, a slide (not shown), is arranged in the handle body 11, in which the driving member 9 is arranged. As shown in FIG. 2, FIG. 3 and FIG. 4, the driving member 9 may reciprocate along the slide. For example, the clamping assembly 3 may be actuated to close when the driving member 9 moves distally, while to open when the driving member 9 moves proximately. More specifically, for example, the elongated body 2 comprises an inner tube and an outer tube, through which the clamping assembly 3 is actuated to open or close by the driving member 9.

In an alternative embodiment of the present disclosure, the actuation mechanism further comprises a biasing member for against rotation of the second trigger 5. More specifically, the biasing member 6 prevents the second link 7 from moving proximately so as to prevent movement of the second trigger 5 until force applied on the driving member 9 exceeds predetermined limit. For example, as shown in the figures, when the first trigger 4 rotates in a direction indicated by arrow A, forcing the pivot 10 to move upwards, so as to further provide the second link 7 with a trend of moving proximately. Meanwhile, a force in an opposite direction is provided by the biasing member 6, eliminating force delivered to the second trigger 5, so as to further prevent the second trigger 5 from rotating, i.e. holding the second trigger 5. The second trigger 5 may stay stationary until the force delivered thereto exceeds the limit of force provided by the biasing member 6. More specifically, the biasing member 6 can be any elastic member that is capable of providing biasing/opposing force, for example, a compression spring, tension spring, or torsion spring, etc. Arrangement may be designed variously according to various types of the biasing members 6, as long as it can provide opposing force. For example, a compression spring may be arranged in the handle body 11, with two ends engaging with the proximal inner wall of the handle body 11 and the proximal end of the second link 7, respectively. Thus, the compression spring may provide an opposing force against force applied on the second link 7 so as to prevent movement of the second trigger 5.

Hereinafter, engagement and movement of the actuation mechanism will be described in details cooperated with different states of the ultrasonic surgical instrument. FIG. 3 shows a free state (initial state) of the ultrasonic surgical instrument, where the clamp assembly is open and the actuation mechanism is under no forces. Now referring to FIG. 4, when the first trigger 4 is rotated in a direction indicated by arrow A about a first pivot 41, the pivot 10 may be forced to move upwards, where the value of the angle formed by the first link 8 and the second link 7 is increased. Since the second link 7 is limited by the biasing member 6 from moving proximately, the pivot 10 may actuate the first link 8 to move distally during the upward movement thereof, so as to further actuate the driving member 9 to move distally for closing the clamping assembly 3.

FIG. 4 shows the state of the ultrasonic surgical instrument of one embodiment of the present disclosure, where the clamping assembly 3 is fully closed. It can be shown in FIG. 3 and FIG. 4 that the second trigger 5 is prevented from further movement by the biasing member 6, for example, the compression spring, so that the driving member 9 is pushed distally by the first link 8 for closing the clamping assembly 3.

Figure 5:
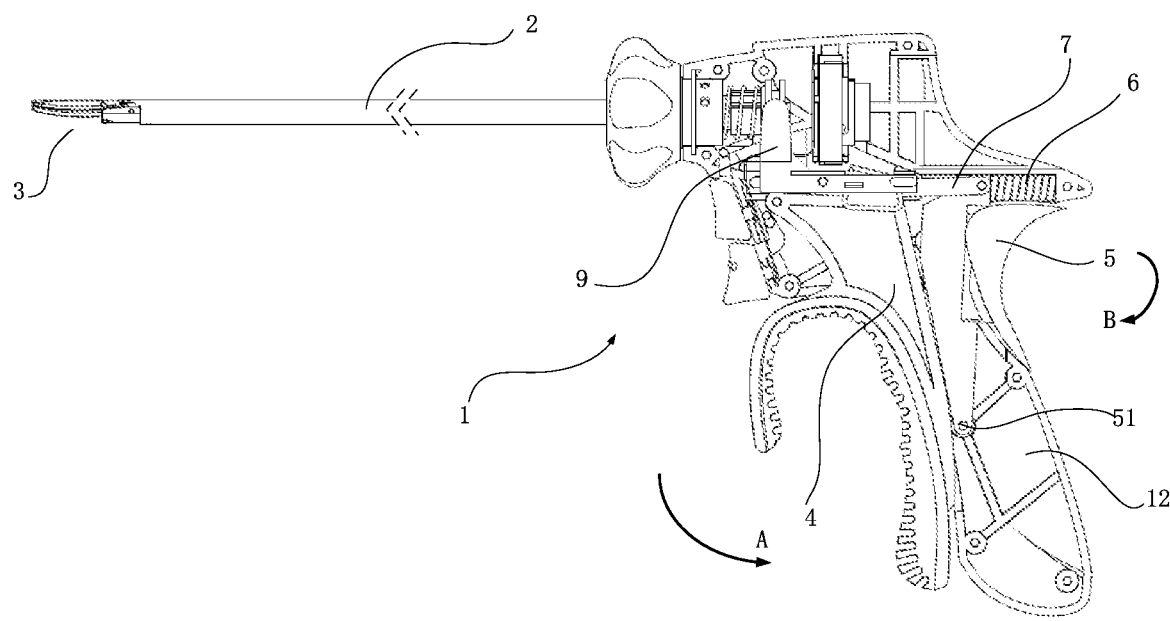
FIG. 5 illustrates schematic view of the ultrasonic surgical instrument of one embodiment of the disclosure, with the second trigger being rotated.

After the clamping assembly is closed, as shown in FIG. 5, the first trigger 4 is further rotated in the direction indicated by arrow A. The second trigger 5 may rotate about a second pivot 51 in a direction indicated by an arrow B in FIG. 5 when force delivered to the second link 7 through the driving member 9, the pivot 10 and the first trigger 4 exceeds the maximum opposing force provided by the biasing member 6. Here, the operator may receive a feedback of force on the second trigger 5, so he/she can know the clamping force applied on the clamping assembly. The operator may further apply additional force on the second trigger 5, which may be further delivered to the first link 8 for pushing the driving member 9 through the second trigger 5, the second link 7 and the pivot 10, eventually increasing the clamping force on the clamping assembly 3. By using the actuation mechanism of one of the embodiments of the present disclosure, forces applied on both first and second triggers 4, 5 may be delivered together to the clamping assembly, so that the clamping force thereof is increased. Thus, comparing with an ultrasonic surgical instrument of prior art having only one trigger, the clamping assembly may be employed for wider range by applying forces on two triggers, so as to abroad applications of the ultrasonic surgical instrument.

More specifically, the angle formed by the first link 8 and the second link 7 is less than 180°, and during rotation of the first trigger 4 and/or the second trigger 5 in directions indicated by arrows A, B, the angle formed therebetween increases but less than 180°. In another word, when the first trigger 4 and the second trigger 5 move to their limited positions, respectively, the angle therebetween is less than 180°. Alternatively, it is preferred that the angle formed by the first link 8 and the second link 7 is within a range of 60° to 150° when the first trigger 4 and the second trigger 5 are in free state, i.e. under no forces, for example, the angle could be 60°, 70°, 80°, 490°, 100°, 110°, 120°, 130°, 140°, or 150°, or any value between 60° and 150°. When the first trigger 4 and the second trigger 5 are in their limited positions, respectively, the angle therebetween is less than 180°, for example, 175°, or 170°.

It is preferred that the length of the first link 8 is designed less than that of the second link 7, so that more horizontal components of forces applied on the first trigger 4 and the second trigger 5 can be delivered to the first link 8 for actuating the driving member 9 to move distally.

As an alternative embodiment, the actuation mechanism further comprises an off-center member, through which the mechanical advantage mechanism is actuated by the first trigger 4. More specifically, the off-center member is arranged on the first trigger 4, which may be actuated to rotate through rotation of the first trigger 4, and further actuate the mechanical advantage mechanism to move.

Furthermore, in an alternative embodiment, a plurality of flutes are provided for the first trigger 4 for being grasped by the index fingers of the operator, and a curved portion is provided for the second trigger 5, configured for better contacting with the portion between the thumb and the index finger of the operator, such that the operator may apply forces more comfortable, as shown in FIG. 2.

For improving stability of the actuation mechanism during movement, in one embodiment of the present disclosure, a sliding member is further provided for engaging the first trigger assembly and the second trigger assembly. For example, a sliding aperture is arranged in the first trigger 4, as shown in FIG. 2, the pivot pin 10 is slidably disposed within the aperture 42. Referring to both FIG. 3 and FIG. 4, no matter how the first trigger 4 and/or the second trigger moves, the pivot pin 10 may stay within the aperture 42. Specifically, the pivot pin 10 slides within the aperture 42 during the movement of the first trigger 4 from its free state shown in FIG. 3 to the under-force state shown in FIG. 4, and the position where the pivot pin 10 contacts with the first trigger 4 may also change during rotation of the first trigger 4 and/or the second trigger 5. However, the pivot pin 10 may always disposed in the aperture 42 so as to maintain engagement between the pivot pin 10 and the first trigger 4 during rotation of the first trigger 4. In addition, a recovering spring may also be arranged in the first trigger 4, configured for forcing the first trigger 4 to recover to its initial position. For example, a twist spring may be arranged so as to force the first link 8 and the second link 7 to the initial position through the aperture 42.

Figure 6:
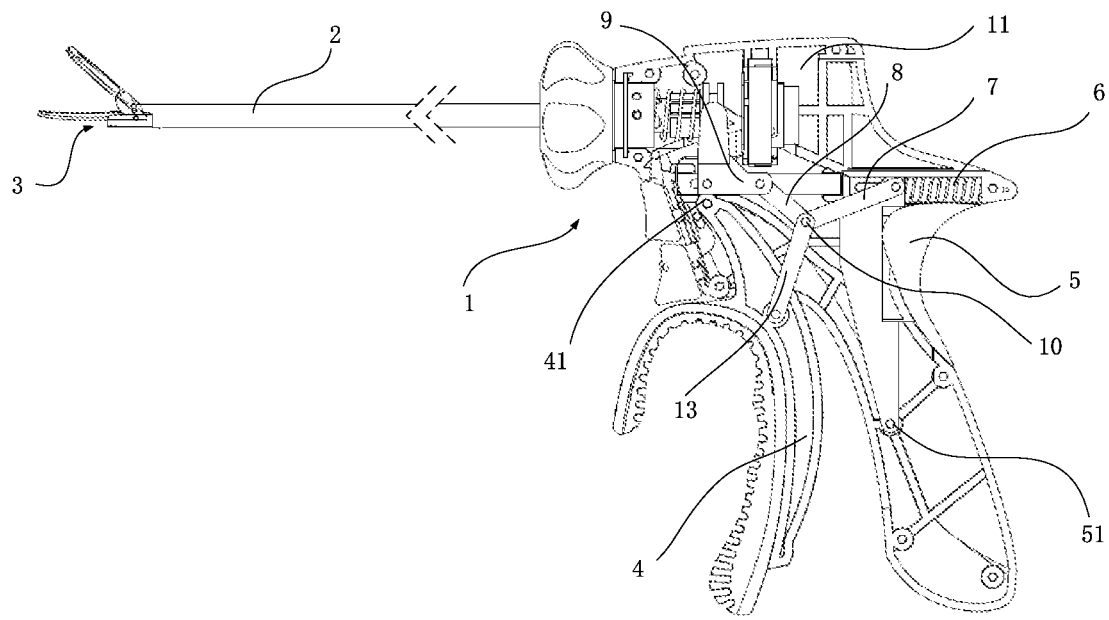
FIG. 6 illustrates an ultrasonic surgical instrument of another embodiment of the present disclosure, in free state.

Alternatively, further referring to FIG. 6, one end of the third link 13 is engaged with the first trigger 4 and the other end thereof is engaged with the first link 8 and the second link 7, respectively. The other end of the second link 7 is engaged with the second trigger 5 and the other end of the first link 8 is engaged with the driving member 9. In one embodiment of the present disclosure, a sliding member is provided in the handle body 11, for example, a slide configured to receive the driving member 9 for sliding therein. As shown in FIG. 2, FIG. 3 and FIG. 4, the driving member 9 may reciprocate along the slide. For example, the clamping assembly 3 may be actuated to close when the driving member 9 moves distally, and may be actuated to open when the driving member 9 moves proximately. When the first trigger 4 is rotated about the first pivot 41 in the direction indicated as arrow A in FIG. 6, the third link 13 is forced to move so as to actuate movement of the first link 8 and the driving member 9. It is preferred that a biasing member 6 may be provided in the embodiment, such as, a compress spring. The biasing member 6 is arranged to be against the inner wall of the proximate portion of the handle body 11 and the proximate end of the second link 7, respectively, which has the similar function as the biasing member 6 described in the above mentioned embodiments, thus details will not be described here again.

Similarly, engagement and movement of the actuation mechanism of the above mentioned embodiment will be described in details incorporated with various working states of the ultrasonic surgical instrument in one of the embodiments of the present disclosure as shown in figures.

FIG. 6 shows the ultrasonic surgical instrument of one embodiment of the present disclosure in the free state, where the actuation mechanism comprises the first link 8, second link 7 and the third link 13; one end of the first link 8, the second link 7 and the third link 13 is engaged with each other, respectively, and the other end of the first link 8 is engaged with the sliding member, for example, the other end of the first link 8 is engaged with the slide arranged in the rack in engagement with the driving member 9. The proximate end of the second link 7 is engaged with the second trigger 5, and the other end of the third link 13 is engaged with the first trigger 4. Thus, the third link 13 is forced to move through movement of the first trigger 4, as shown in FIG. 6 and FIG. 7, and the three links form a shape like Y.

Figure 7:
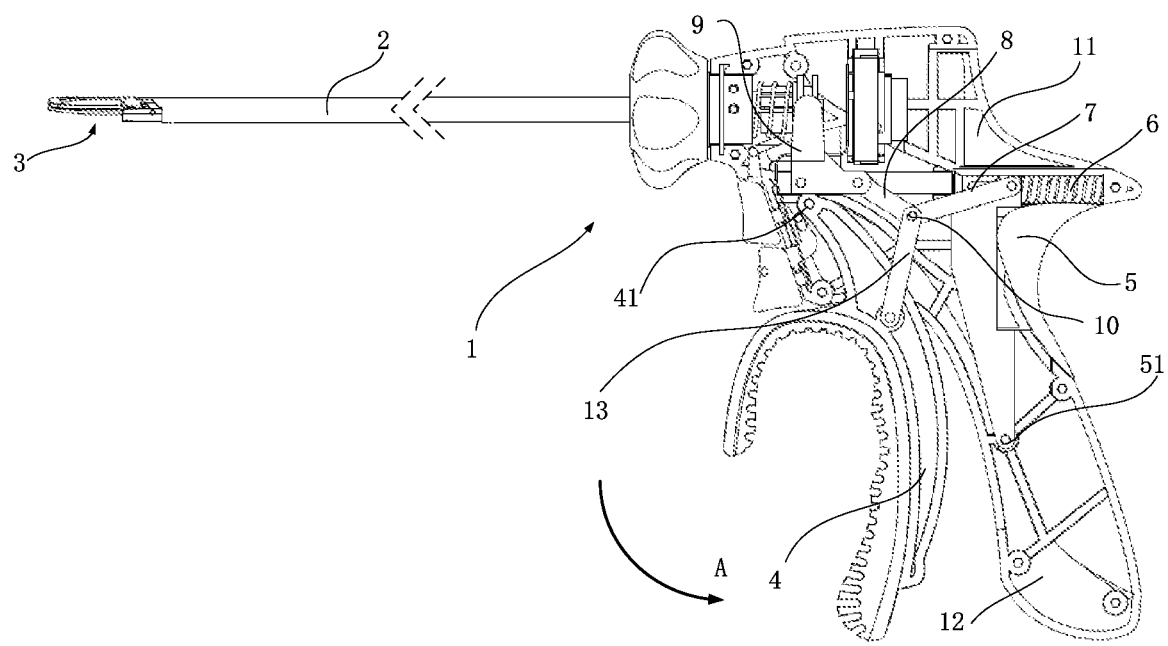
FIG. 7 illustrates schematic view of the ultrasonic surgical instrument of another embodiment, with the clamping assembly closed.

Rotating the first trigger 4 in the direction indicated by arrow A, so as to close the clamp assembly 3 disposed at the distal portion of the ultrasonic surgical instrument, as shown in FIG. 7, since force delivered to the second trigger 5 through the second link 7 has not exceeded maximum opposing force provided by the biasing member 6, the second trigger 5 may not move accordingly. Thus, the third link 13 is forced to move upwards by the first trigger 4 so as to further push the first link 8 to move distally together with the driving member 9, for closing the clamp assembly 3.

Figure 8:
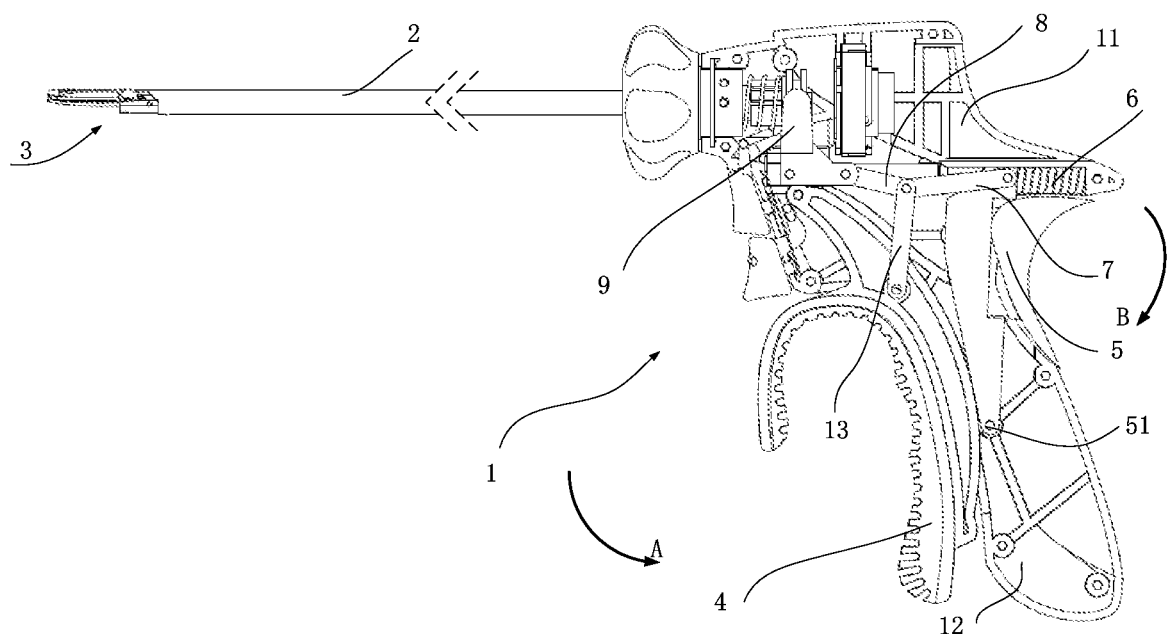
FIG. 8 illustrates schematic view of the ultrasonic surgical instrument of another embodiment of the disclosure, with the second trigger being rotated.

Further rotating the first trigger 4, as shown in FIG. 8, when the force delivered to the second trigger 5 through the second link 7 exceeds the maximum opposing force of the biasing member 6, the biasing member 6 may be compressed so as to actuate the second link 7 forcing the second trigger 5 to rotate about the second pivot 51 in the direction indicated by arrow B. Then force applied on the second trigger 5 may be provided back to the user, so that the user may feel the clamping force of the clamp assembly. Furthermore, the user may also apply force on the second trigger 5, for example, using the portion between thumb and index finger to push the second trigger 5, and then the force applied on the second trigger 5 may be further delivered to the second link 7 so as to further apply force on the clamp assembly through the first link 8 and the driving member 9, which may increase the clamping force applied on the closed clamp assembly. Thus, by pushing both the first trigger 4 and the second trigger 5, a combined force will be delivered to the clamp assembly through the actuation mechanism of one embodiment of the present disclosure, such that the clamping force may be increased.

As an alternatively embodiment, the first link 8, the second link 7 and the third link 13 of the above described embodiment may be designed as an off-center mechanism. More specifically, during the upward movement of the pivot pin 10, it may further move even when the first link 8 and the second link 7 are forming a line, which means, the angle formed by the first link 8 and the second link 7 increases during the movement of the actuation mechanism, and may exceed 180°.

As an alternative embodiment of the present disclosure, referring to FIG. 9, FIG. 10 and FIG. 11, the actuation mechanism has a similar structure as that of the previous described embodiments, except for the arrangement of the second trigger 5, for example, the location of the second trigger 5. For better describing the second trigger 5 of the embodiment, the other members will not be described in details again. As shown in FIG. 9, the second trigger 5 is arranged inside the handle body 11, and the biasing member 6, such as a compress spring, is arranged in a slot disposed in the second trigger 5. A stop (not shown) is further arranged in the handle body 11, configured to be contacted against one end of the biasing member 6, while the other end of the biasing member 6 contacts against an inner wall of the slot of the second trigger 5.

FIG. 9 shows the ultrasonic surgical instrument of the above described embodiment in free state. Rotating the first trigger 4 in the direction indicated by arrow A, so as to close the clamp assembly 3 at the distal portion of the ultrasonic surgical instrument, as shown in FIG. 10, and the second trigger 5 may not be forced to move together with the first trigger 4 until the force delivered thereon exceeds the maximum opposing force provided by the biasing member 6. Here, the third link 13 is forced to move upwards by the first trigger 4 and then pushes the first link 8 and the driving member 9 to move distally, for closing the clamp assembly 3.

Further rotating the first trigger 4, as shown in FIG. 11, the biasing member 6 may be compressed when the force applied thereon through the second link 7 and the second trigger 5 exceeds the opposing force thereof, so that the second trigger 5 is actuated to rotate about the second pivot 51 in the direction indicated by arrow B by the second link 7. As shown in FIG. 9, FIG. 10 and FIG. 11, the first trigger 4 further comprises a protrusion 43, when the protrusion 43 of the first trigger 4 contacts with the second trigger 5, further rotating the first trigger 4, the second trigger 5 will be actuated to rotate counterclockwise about the second pivot 51 under the pressure of the protrusion 43, such that, the driving member 9 may be further actuated to move distally through the second link 7 and the first link 8 for increasing clamping force on the clamp assembly after being closed.

As an alternative embodiment, furthermore, the second trigger 6 is engaged with the first link 8 through a cam, through which the first trigger 4 is engaged with the second link 7. More specifically, the cam is rotated with rotation of the first trigger 4, which may further actuate the first link 8 and the driving member 9 to move.

Moreover, in the above mentioned embodiment, a mechanical advantage mechanism and the second trigger 5 are provided for giving clamping force feedback to the operator. Thus during operation, clamping force on the clamp assembly may be provided back to the user directly and accurately via the second trigger 5, which may help the user to adjust the force applied on the clamp assembly accordingly, avoiding damages to tissues caused by excessive clamping force. Additionally, through the arrangement of the double trigger, the user may know the actual condition of the clamped tissue or vessel so as to adjust forces applied on the clamp assembly, which may expend applications of the ultrasonic surgical instruments.

Evidently those skilled in the art can make various modifications and variations to the present disclosure without departing from scope of the present disclosure. Thus the present disclosure is also intended to encompass these modifications and variations thereto so long as the modifications and variations come into the scope of the claims appended to the present disclosure and their equivalents.

I claim:

1. An actuation mechanism for performing an action, wherein, said actuation mechanism comprises:
    a first movable trigger assembly having a first trigger;
    a second movable trigger assembly have a second trigger,
        wherein said first trigger is movable independently with respect to said second trigger during a portion of movement of said first trigger and/or said second trigger; and a driving member in engagement with said first trigger assembly and said second trigger assembly, respectively, wherein, said first trigger assembly and said second trigger assembly are applied different mechanical advantages;

said actuation mechanism further comprises a bias member configured for stopping said second trigger assembly until force against said driving member exceeds a predetermined limit;

wherein said force against said driving member is from said first trigger assembly;

wherein said first trigger assembly is engaged with said second trigger assembly through a sliding member.

2. The actuation mechanism according to claim 1, wherein said mechanical advantage of said second trigger assembly is determined by position of said first trigger assembly.

3. The actuation mechanism according to claim 1, wherein, movement of said first trigger depends on movement of said second trigger during a portion of movement thereof.

4. The actuation mechanism according to claim 1, further comprising an off-center member, through which said driving member is actuated by said first trigger assembly.

5. The actuation mechanism according to claim 1, wherein, said first trigger is engaged with said driving member through a first link, and said second trigger is engaged with said driving member and said first link through a second link.

6. An ultrasonic surgical instrument comprises an actuation mechanism, wherein, said actuation mechanism comprises:

a first movable trigger assembly having a first trigger;

a second movable trigger assembly have a second trigger, wherein said first trigger is movable independently with respect to said second trigger during a portion of movement of said first trigger and/or said second trigger; and a driving member in engagement with said first trigger assembly and said second trigger assembly, respectively, wherein, said first trigger assembly and said second trigger assembly are applied different mechanical advantages;

said actuation mechanism further comprises a bias member configured for stopping said second trigger assembly until force against said driving member exceeds a predetermined limit; wherein said force against said driving member is from said first trigger assembly;

wherein said first trigger assembly is engaged with said second trigger assembly through a sliding member.

7. The ultrasonic surgical instrument according to claim 6, wherein said mechanical advantage of said second trigger assembly is determined by position of said first trigger assembly.

8. The ultrasonic surgical instrument according to claim 7, wherein, further comprises:

a handle portion for being held by an operator; and a clamping assembly engaged with said driving member through an elongated shaft, which is adapted to clamp tissue.

9. The ultrasonic surgical instrument according to claim 8, wherein, said clamping assembly is rotatable about a longitudinal axis with respect to said handle portion.

10. The ultrasonic surgical instrument according to claim 8, wherein, said first trigger and said second trigger are arranged on opposing sides of said handle portion, respectively, at least one of which are contactable by said operator.

11. The ultrasonic surgical instrument according to claim 10, wherein, said second trigger assembly is further adapted for providing feedback to said operator of force on said driving member.

12. The ultrasonic surgical instrument according to claim 6, wherein, during a portion of movement of said first trigger, said second trigger rotates in direction opposite to said first trigger.

13. The ultrasonic surgical instrument according to claim 6, wherein, during a portion of movement of said first trigger, said second trigger rotates in same direction as said first trigger.

14. An actuation mechanism for performing action, wherein, said actuation mechanism comprises:

a first movable trigger assembly having a first trigger;

a second movable trigger assembly having a second trigger, wherein, said first trigger is movable independently with respect to said second trigger during a portion of movement of said first trigger and/or said second trigger;

a driving member in engagement with said first trigger assembly and said second trigger assembly, respectively; and a first link, through which said second trigger assembly is engaged with said driving member;

said actuation mechanism further comprises a bias member configured for stopping said second trigger assembly until force against said driving member exceeds a predetermined limit; wherein said force against said driving member is from said first trigger assembly;

wherein said first trigger assembly is engaged with said second trigger assembly through a sliding member.

15. The actuation mechanism according to claim 14, wherein, further comprises a second link, through which said second trigger is engaged with said first link.

16. The actuation mechanism according to claim 14, wherein, said second trigger assembly is engaged with said first link through the sliding member.

17. The actuation mechanism according to claim 15, wherein, said second trigger is engaged with said first link through a third link.

18. The actuation mechanism according to claim 14, wherein, further comprises an off-center member, through which said driving member is actuated by said first trigger assembly.

\* \* \* \* \*